(12) United States Patent
Zhao et al.

(10) Patent No.: US 11,482,307 B2
(45) Date of Patent: Oct. 25, 2022

(54) MULTI-TEMPORAL INFORMATION OBJECT INCREMENTAL LEARNING SOFTWARE SYSTEM

(71) Applicant: Drexel University, Philadelphia, PA (US)

(72) Inventors: Zhengqiao Zhao, Philadelphia, PA (US); Gail Rosen, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 1241 days.

(21) Appl. No.: 15/910,845

(22) Filed: Mar. 2, 2018

(65) Prior Publication Data

US 2018/0253529 A1 Sep. 6, 2018

Related U.S. Application Data

(60) Provisional application No. 62/465,919, filed on Mar. 2, 2017.

(51) Int. Cl.
| | |
|---|---|
| *G16B 50/10* | (2019.01) |
| *G06K 9/62* | (2022.01) |
| *G16B 50/00* | (2019.01) |
| *G16B 40/00* | (2019.01) |
| *G16B 40/30* | (2019.01) |
| *G06F 16/28* | (2019.01) |
| *G16B 40/20* | (2019.01) |
| *G16B 50/30* | (2019.01) |

(52) U.S. Cl.
CPC .......... *G16B 50/10* (2019.02); *G06F 16/285* (2019.01); *G06K 9/6256* (2013.01); *G06K 9/6278* (2013.01); *G16B 40/00* (2019.02); *G16B 40/20* (2019.02); *G16B 40/30* (2019.02); *G16B 50/00* (2019.02); *G16B 50/30* (2019.02)

(58) Field of Classification Search
CPC ........ G16B 50/10; G16B 40/00; G16B 40/30; G16B 40/20; G16B 50/00; G16B 50/30; G06F 16/285; G06K 9/6256; G06K 9/6278

See application file for complete search history.

(56) References Cited

U.S. PATENT DOCUMENTS

| | | | | |
|---|---|---|---|---|
| 10,042,976 B2 * | 8/2018 | Colwell | ............. | G16B 30/20 |
| 11,200,503 B2 * | 12/2021 | Medlock | ............. | G06N 20/00 |
| 2016/0132640 A1 * | 5/2016 | Layer | ............. | G16B 20/00 |
| | | | | 706/12 |

OTHER PUBLICATIONS

Levin, Wiley, 2012, pp. 1030-1047.*
Exploratory Learning, Dalvi, 2013.*

(Continued)

*Primary Examiner* — Waseem Ashraf
*Assistant Examiner* — Michael I Ezewoko
(74) *Attorney, Agent, or Firm* — Schott, P.C.

(57) ABSTRACT

An incremental author disambiguation framework may create new clusters to accommodate new data based on the existing cluster results and newly added data. The proposed system may provide frequent update of taxonomic classification, name disambiguation and many other applications because it takes less time to generate new results. In addition, the proposed methods may reduce the time needed for updating the model and help improve the performance with the limited computational resource.

10 Claims, 10 Drawing Sheets

(56) References Cited

OTHER PUBLICATIONS

Incremental Learning of Concept Drift in Nonstationary Environments, Elwell, 2011, pp. 1517-1531.*
Kang, 2015, pp. 1-15.*
Krawczyk, 2017, pp. 132-156.*
Semi-Supervised Learning, Chapelle, 2006, chapters 1-3, chapter 9.*
Tsukioka, 2014, IEEE, pp. 1591-1596.*
Ultrafast metagenomic sequence, Kraken, 2012 pp. 1-12.*
Amazon Web Services (AWS), "Amazon EC2 Pricing," Accessed on Mar. 5, 2018, https://aws.amazon.com/ec2/pricing/on-demand/.
Carvalho, et. al, "Incremental Unsupervised Name Disambiguation in Cleaned Digital Libraries," Journal of Information and Data Management, vol. 2, No. 3, Oct. 2011, pp. 289-304, Accessed on Mar. 5, 2018, https://pdfs.semanticscholar.org/eda7/f8ea8f15a958a330c76a8b704c2acf7dc2d4.pdf.
Levin et. al, "Citation-based bootstrapping for large-scale author disambiguation," Journal of the American Society for Information Science and Technology, vol. 63, Issue 5, pp. 847-1058, Published Feb. 14, 2012, Accessed on Mar. 5, 2018, http://onlinelibrary.wiley.com/doi/10.1002/asi.22 621/abstract.
Santana, et. al, "Incremental author name disambiguation by exploiting domain-specific heuristics," Journal of the Association for Information Science and Technology, 68: 931-945, Published Dec. 21, 2016, Accessed on Mar. 5, 2018, http://onlinelibrary.wiley.com/doi/10.1002/asi.23726/abstract.
The Economist, "After Moore's Law | Technology Quarterly." Last updated on Feb. 25, 2016, Accessed on Mar. 5, 2018, www.economist.com/technology-quarterly/2016-03-12/after-moores-law.
Wetterstrand, K, "DNA Sequencing Costs: Data from the NHGRI Genome Sequencing Program (GSP)," National Human Genome Research Institute (NHGRI), Last updated on Oct. 31, 2017, Accessed on Mar. 5, 2018, https://www.genome.gov/sequencingcostsdata/.
Wood and Salzberg, "Kraken: ultrafast metagenomic sequence classification using exact alignments," Genome Biology, Published on Mar. 3, 2014, Accessed on Mar. 5, 2018, http://genomebiology.com/2014/15/3/R46.
Zhao, et. al, "Incremental Author Name Disambiguation for Scientific Citation Data," Data Science and Advanced Analytics (DSAA), 2017 IEEE International Conference on Data Science and Advanced Analytics (DSAA), Added to IEEE on Jan. 18, 2018, Accessed on Mar. 5, 2018, http://ieeexplore.ieee.org/document/8259776/?reload=true.
Levin, et. al, "Citation-Based Bootstrapping for Large-Scale Author Disambiguation," Journal of the American Society for Information Science and Technology, 63(5):1030-1047, Published on Feb. 14, 2012, Accessed on Mar. 5, 2018, https://nlp.stanford.edu/pubs/levin2012.pdf.
Frey and Dueck, "Clustering by Passing Messages Between Data Points," Science Magazine, vol. 315, Published on Feb. 16, 2007, accessed on Mar. 7, 2018, http://www.psi.toronto.edu/affinitypropagation/FreyDueckScience07.pdf.
Sun and Guo, "Incremental Affinity Propagation Clustering Based on Message Passing," IEEE Transactions on Knowlege and Data Engineering, vol. 26, No. 11, Published on Nov. 2014, Accessed on Mar. 7, 2018, https://www.researchgate.net/publication/273393288_Incremental_Affinity_Propagation_Clustering_Based_on_Message_Passing.
Dalvi, et. al, "Exploratory Learning," School of Computer Science, Carnegie Mellon University, Submitted on Jul. 1, 2013, Accessed on Mar. 7, 2018, http://www.cs.cmu.edu/~bbd/bbd_ecml13.pdf.
G, Rosen et. al. "Metagenome fragment classification using N-mer frequency profiles," Adv Bioinformatics, Published on Nov. 16, 2008, Accessed on Mar. 7, 2018, https://www.ncbi.nlm.nih.gov/pubmed/19956701.
Xia, et. al, "Local and global approaches of affinity propagation clustering for large scale data," Journal of Zhejiang University-SCIENCE A, vol. 9, Issue 10, Published on Oct. 2008, Accessed on Mar. 8, 2018, https://link.springer.com/article/10.1631/jzus.A0720058.

* cited by examiner

Algorithm 1 CBBEM

```
 1: procedure CBBEM(X_labeled, X_unlabeled, label)
 2: E-step:
 3:     X ← [X_labeled; X_unlabeled]
 4:     θ^(0) ← NBC_train(X_labeled, label)
 5:     AICc_SCORE ← AICc(θ^(0), X)
 6:     while !Convergence(AICc_SCORE) do
 7:         AICc_SCORE_old ← AICc(θ^(t), X)
 8:         undetermined ← [ ]
 9:         for x in X_unlabeled do
10:             posterior ← NBC_test(x, θ^(t))
11:             if Newclass(posterior) then
12:                 undetermined ← [undetermined; x]
13:         if size(undetermined) > 0 then
14:             newclusters ← unsupervised-clustering(undetermined)
15:             newcluster ← densest(newclusters)
16:             θ^(t+1) ← NBC_train([X_labeled, newcluster], [label, newclass])
17:         else
18:             θ^(t+1) ← θ^(t)
19:         posteriors ← NBC_test(X_unlabeled, θ^(t+1))
20: M-step:
21:         AICc_SCORE_new ← AICc(θ^(t+1), X)
22:         if AICc_SCORE_new < AICc_SCORE_old then
23:             [X_confi, posteriors_confi] ← Subset_of_Confidence(X_unlabeled, posteriors)
24:             θ^(t+1) ← NBC_train([X_labeled; X_confi], [label; posteriors_confi])
25:             AICc_SCORE ← AICc_SCORE_new
26:         else
27:             θ^(t+1) ← θ^(t)
28:             AICc_SCORE ← AICc_SCORE_old
```

FIG. 6

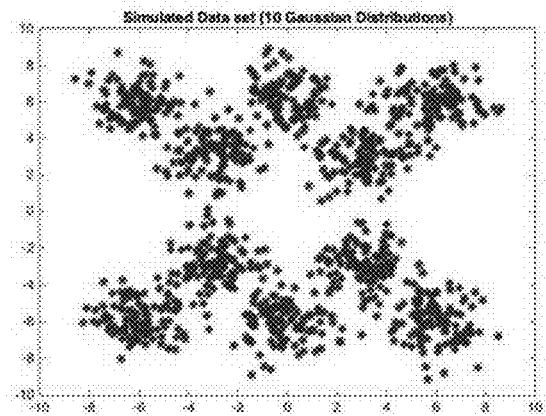

FIG. 7A

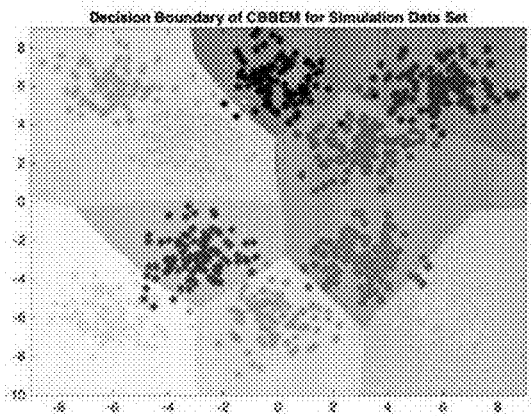

FIG. 7B

MULTI-TEMPORAL INFORMATION OBJECT INCREMENTAL LEARNING SOFTWARE SYSTEM

STATEMENT REGARDING GOVERNMENT SUPPORT

This invention was made with government support under Contract No. IIP-1160960 awarded by the National Science Foundation. The government has certain rights in the invention.

BACKGROUND

Big data analysis creates big data challenges. These include maintaining and updating indexes and data clusters that permit efficient and accurate data access. In the metagenomics field as an example. One of the main challenge in metagenomics is to answer, "What is here?", i.e., identify the microorganism in the sample. Taxonomic classification on DNA sequences is helpful to assist the researcher with this problem. Taxonomic classification, however, suffers from model updating problems. That is, new strains and species are discovered and added to the database frequently. The cost of sequencing a genome is out-pacing Moore's law (FIG. 2). Thus, more and more new species or strains are discovered and sequenced. Moreover, Moore's law has not applied in the past few years (FIG. 3).

In other words, in contrast to the growth of the number of (meta)genomes being added to databases, the computational speed to process them is not increasing at the same rate. Thus, it is more and more computationally intensive to reprocess the whole National Center for Biotechnology Information (NCBI) Genomes database and update the classifier when the database is updated. FIGS. 4 and 5 show the growth of completed bacterial genomes in NCBI. FIG. 4 shows that the total number of complete genomes keeps increasing over the past 18 years. FIG. 5 shows the number of complete genomes being added to the database per year. As shown, there are more and more new genomes being added to the database.

While presented in the field of genomics, the challenge in that field is not unique and the invention described herein is not sol limited. Other big data challenged fields like social media, financial transactions, recommendation systems, as well as others, may face the same challenge.

SUMMARY OF THE EMBODIMENTS

An algorithm and software system solution that interprets, disambiguates, classifies, enriches, and categorizes digital informational samples such as ontologies, DNA sequences, manuscripts, affiliations, etc. The system optimizes the collection, organization, and linking of granular data elements of electronic information for use in any field that has large data sets. The system is modular and flexibly-designed to leverage automated and manual data ingestion, cleansing, and linking operations. Using advanced supervised and unsupervised machine-learning techniques, the system can automatically (or semi-automatically with minimal human intervention) update itself when new data are available and implement classification during this process, the system can discover novel classes and assign pseudo-labels to the samples that are associated with them.

This incremental learning framework may create new clusters to accommodate new data based on existing cluster results and newly added data. The methods can reduce the time of classification using the existing classification result to help improve the performance with the limited computational resource. Said another way, the method herein improves the computer hardware's performance. Hence the proposed system may provide frequent update of the classification results because it takes less time to generate new results.

The system architecture comprises the following elements: 1) initialize the incremental learner with existing data, 2) generate classification results, 3) update the incremental learner with new data and detect novel classes during this process and assign relevant samples with pseudo labels and 4) use the updated incremental learner to update the classification result based on new data.

The system can incrementally update the incremental learner and classification result as a batch update of new data are added (where the old system should be trained every time). A novel classes detector is optional and is subject to the use cases. Parameters can be tweaked by user to control the sensitivity of such detector.

The method and system herein use an incremental learning framework and may update itself and create new clusters to accommodate new data based on the existing cluster results and newly added data instead of re-processing the whole database. In addition, the system may leave samples unclassified if there is little evidence to support the classification result until additional data points arrive in the model and support the classification decision. Second, preferred embodiments and example use cases included a flexible and modular software system—with the methods as core components—that enables scalable automatic or semi-automated adjustments to key time scales and data parameters on which classification/disambiguation and other processes are performed.

The proposed system may provide more frequent updates of classification results while taking less time to generate new results. In addition, the proposed methods can reduce the number of iterations of convergence needed for the existing clustering method to help improve the performance with limited computational resources. As well, the system could integrate with established classification/disambiguation systems to augment and extend their power.

The system could be readily leveraged by companies in many vertical markets that depend on accurate understanding of large and expanding digital datasets. It could be deployed as a stand-alone or integrated software component in many standard programming languages and development frameworks. Preliminary experiments on real-world data and problems have shown its efficacy in scholarly communication analysis and bioinformatics research.

BRIEF DESCRIPTION OF THE DRAWINGS

FIG. 6 shows the pseudo code of one of the proposed methods, CBBEM.

FIG. 7A shows a simulated data set that contains 1000 two-dimensional samples drawn from 10 Gaussian distributions.

FIG. 7B shows the decision boundary created by one of the proposed methods, CBBEM.

DETAILED DESCRIPTION OF THE EMBODIMENTS

A. Hardware Introduction

Figure 1A:
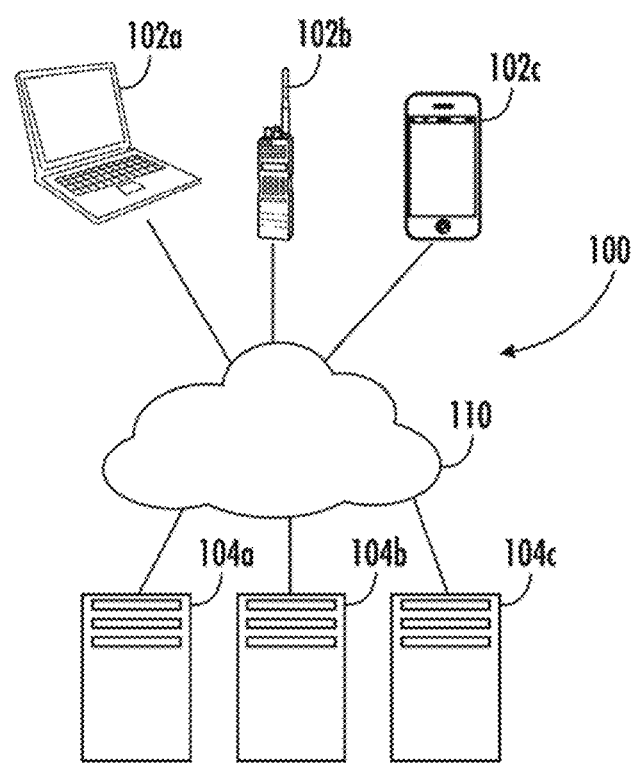
FIG. 1A shows a network diagram of different components of the system.

The system and method described may be implemented using system and hardware elements shown and described herein. For example, FIG. 1A shows an embodiment of a network 100 with one or more clients 102a, 102b, 102c that may be local machines, personal computers, mobile devices, servers, tablets, or virtual reality (VR) headsets that communicate through one or more networks 110 with servers 104a, 104b, 104c. It should be appreciated that a client 102a-102c may serve as a client seeking access to resources provided by a server and/or as a server providing access to other clients.

The network 110 may be wired or wireless. If it is wired, the network may include coaxial cable, twisted pair lines, USB cabling, or optical lines. The wireless network may operate using BLUETOOTH, Wi-Fi, Worldwide Interoperability for Microwave Access (WiMAX), infrared, or satellite networks. The wireless links may also include any cellular network standards used to communicate among mobile devices including the many standards prepared by the International Telecommunication Union such as 3G, 4G, and LTE. Cellular network standards may include GSM, GPRS, LTE, WiMAX, and WiMAX-Advanced. Cellular network standards may use various channel communications such as FDMA, TDMA, CDMA, or SDMA. The various networks may be used individually or in an interconnected way and are thus depicted as shown in FIG. 1A as a cloud.

The network 110 may be located across many geographies and may have a topology organized as point-to-point, bus, star, ring, mesh, or tree. The network 110 may be an overlay network which is virtual and sits on top of one or more layers of other networks.

In most cases, every device on a network has a unique identifier. In the TCP/IP protocol, the unique identifier for a computer is an IP address. An IPv4 address uses 32 binary bits to create a single unique address on the network. An IPv4 address is expressed by four numbers separated by dots. Each number is the decimal (base-10) representation for an eight-digit binary (base-2) number, also called an octet. An IPv6 address uses 128 binary bits to create a single unique address on the network. An IPv6 address is expressed by eight groups of hexadecimal (base-16) numbers separated by colons.

An IP address can be either dynamic or static. A static address remains constant for a system unless modified by a user. Dynamic addresses are assigned by the Dynamic Host Configuration Protocol (DHCP), a service running on the network. DHCP typically runs on network hardware such as routers or dedicated DHCP servers.

Dynamic IP addresses are issued using a leasing system, meaning that the IP address is only active for a limited time. If the lease expires, the computer will automatically request a new lease. Sometimes, this means the computer will get a new IP address, too, especially if the computer was unplugged from the network between leases. This process is usually transparent to the user unless the computer warns about an IP address conflict on the network (two computers with the same IP address).

Another identifier for a device is the hostname. A hostname is a human-readable label assigned to a device and can be modified by a user. Hostname can be resolved to the IP address of the device. This makes hostname a more reliable device identifier in a network with dynamic IP addresses.

Information in the IP Address may be used to identify devices, geographies, and networks. The hostname may be used to identify devices.

A system may include multiple servers 104a-c stored in high-density rack systems. If the servers are part of a common network, they do not need to be physically near one another but instead may be connected by a wide-area network (WAN) connection or similar connection.

Management of group of networked servers may be de-centralized. For example, one or more servers 104a-c may include modules to support one or more management services for networked servers including management of dynamic data, such as techniques for handling failover, data replication, and increasing the networked server's performance.

The servers 104a-c may be file servers, application servers, web servers, proxy servers, network appliances, gateways, gateway servers, virtualization servers, deployment servers, SSL VPN servers, or firewalls.

When the network 110 is in a cloud environment, the cloud network 110 may be public, private, or hybrid. Public clouds may include public servers maintained by third parties. Public clouds may be connected to servers over a public network. Private clouds may include private servers that are physically maintained by clients. Private clouds may be connected to servers over a private network. Hybrid clouds may, as the name indicates, include both public and private networks.

The cloud network may include delivery using IaaS (Infrastructure-as-a-Service), PaaS (Platform-as-a-Service), SaaS (Software-as-a-Service) or Storage, Database, Information, Process, Application, Integration, Security, Management, Testing-as-a-service. IaaS may provide access to features, computers (virtual or on dedicated hardware), and data storage space. PaaS may include storage, networking, servers or virtualization, as well as additional resources such as, e.g., the operating system, middleware, or runtime resources. SaaS may be run and managed by the service provider and SaaS usually refers to end-user applications. A common example of a SaaS application is SALESFORCE or web-based email.

A client 102a-d may access IaaS, PaaS, or SaaS resources using preset standards and the clients 102a-c may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1B:
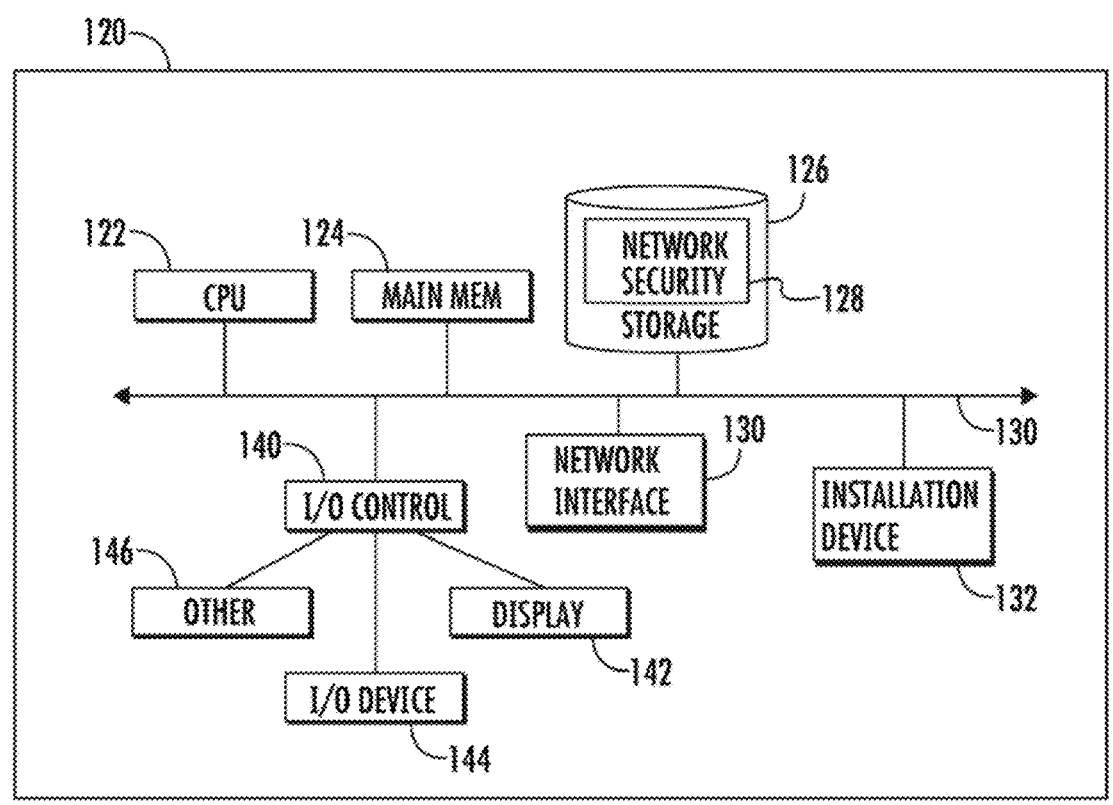
FIG. 1B certain hardware components for use with the system.
Figure 2:
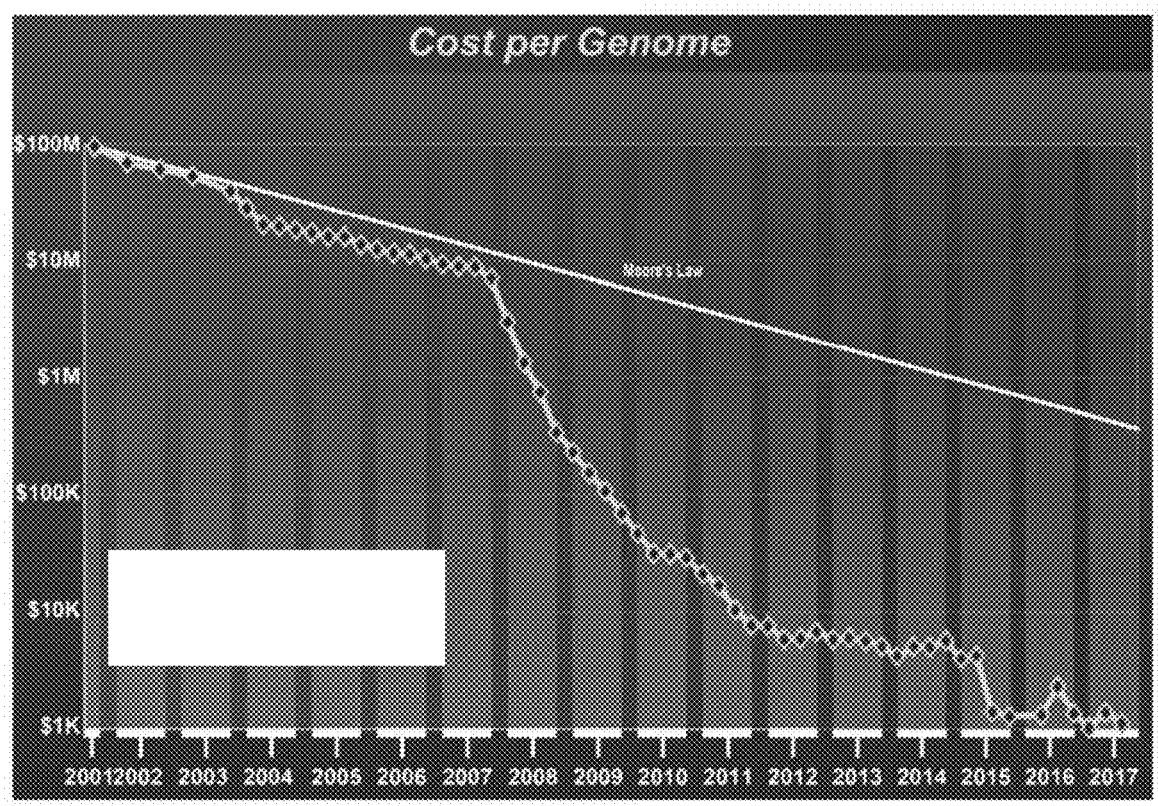
FIG. 2 is a graph showing the cost of sequencing a genome is out-pacing Moore's law.
Figure 3:
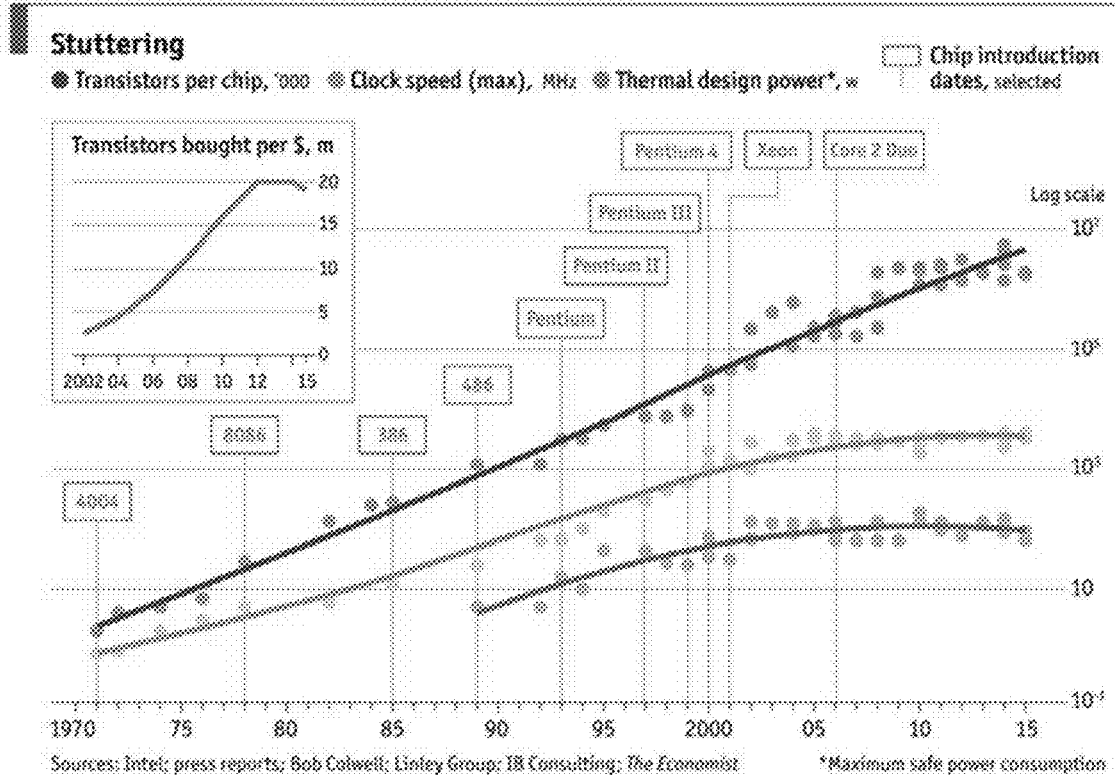
FIG. 3 is a graph showing shows that Moore's law has not applied in the past few years.
Figure 4:
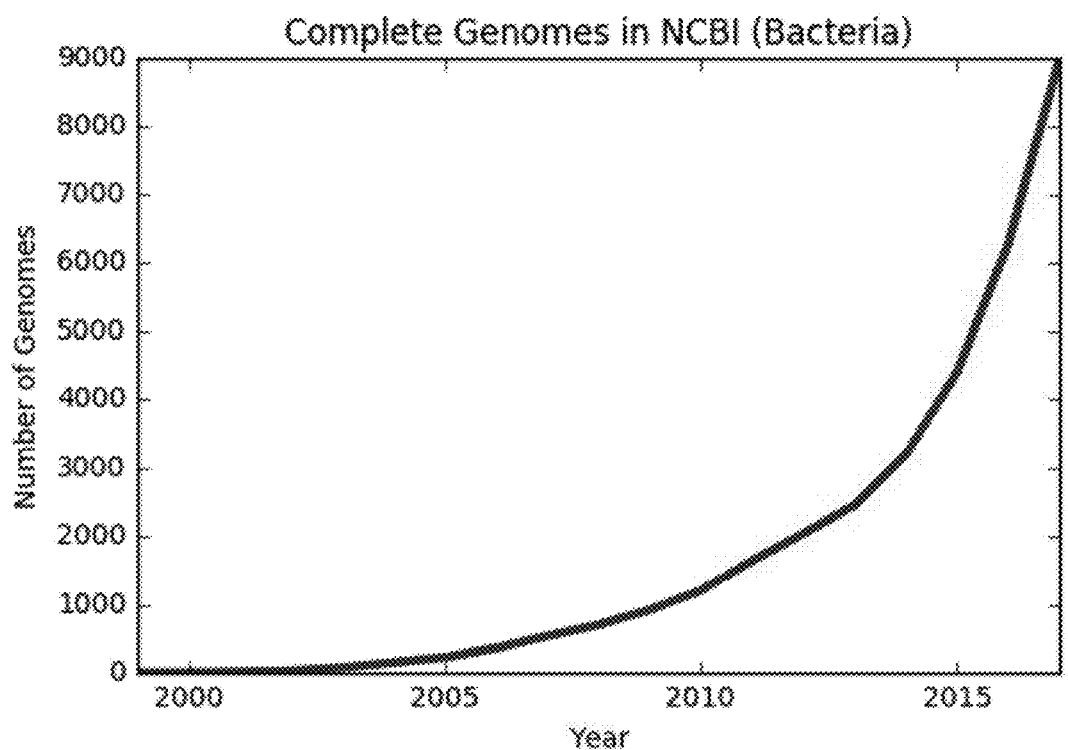
FIG. 4 is a graph showing the number of completed bacterial genomes released in NCBI.
Figure 5:
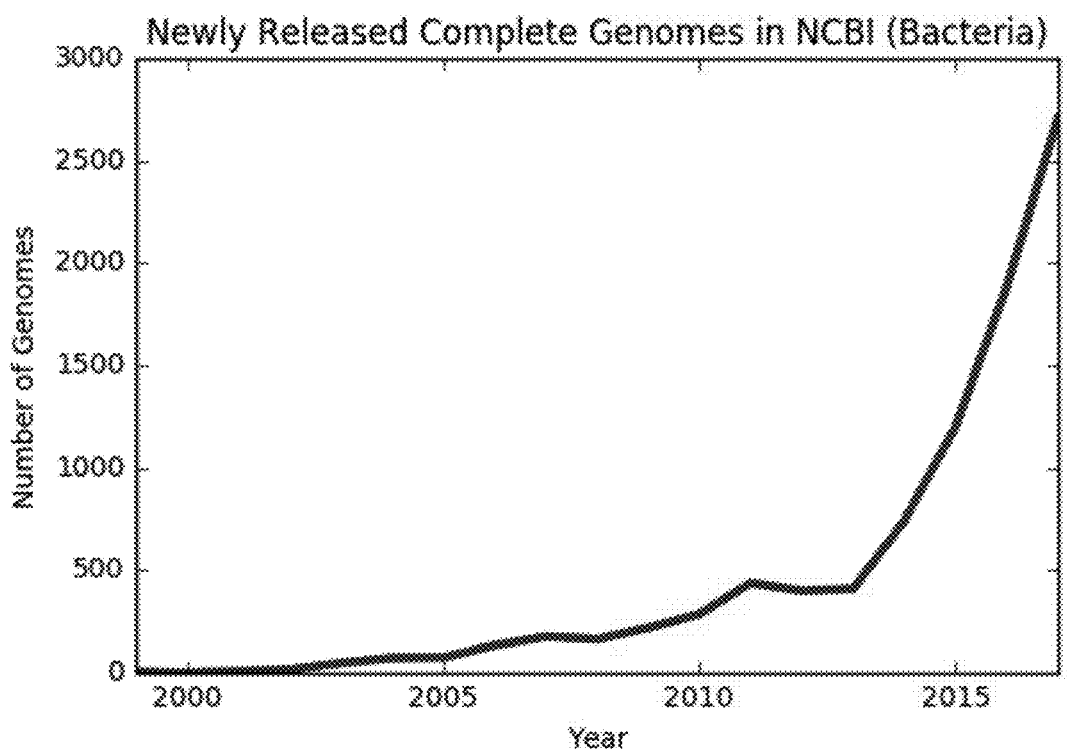
FIG. 5 is a graph showing the number of new released completed bacterial genomes in NCBI every year.

The clients 102a-d and servers 104a-c may be embodied in a computer, network device or appliance capable of communicating with a network and performing the actions herein. FIGS. 1A and 1B show block diagrams of a computing device 120 that may embody the client or server discussed herein. The device 120 may include a system bus 150 that connects the major components of a computer system, combining the functions of a data bus to carry information, an address bus to determine where it should be sent, and a control bus to determine its operation. The device includes a central processing unit 122, a main memory 124, and storage device 124. The device 120 may further include a network interface 130, an installation device 132 and an I/O control 140 connected to one or more display devices 142, I/O devices 144, or other devices 146 like mice and keyboards.

The storage device 126 may include an operating system, software, and a network user behavior module 128, in which may reside the network user behavior system and method described in more detail below.

The computing device 120 may include a memory port, a bridge, one or more input/output devices, and a cache memory in communication with the central processing unit.

The central processing unit 122 may be a logic circuitry such as a microprocessor that responds to and processes instructions fetched from the main memory 124. The CPU 122 may use instruction level parallelism, thread level parallelism, different levels of cache, and multi-core processors. A multi-core processor may include two or more processing units on a single computing component.

The main memory 124 may include one or more memory chips capable of storing data and allowing any storage location to be directly accessed by the CPU 122. The main memory unit 124 may be volatile and faster than storage memory 126. Main memory units 124 may be dynamic random-access memory (DRAM) or any variants, including static random access memory (SRAM). The main memory 124 or the storage 126 may be non-volatile.

The CPU 122 may communicate directly with a cache memory via a secondary bus, sometimes referred to as a backside bus. In other embodiments, the CPU 122 may communicate with cache memory using the system bus 150. Cache memory typically has a faster response time than main memory 124 and is typically provided by SRAM or similar RAM memory.

Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, 3D printers, and VR headsets.

Additional I/O devices may have both input and output capabilities, including haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures.

In some embodiments, display devices 142 may be connected to the I/O controller 140. Display devices may include liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, VR or 3D displays.

The computing device 120 may include a network interface 130 to interface to the network 110 through a variety of connections including standard telephone lines LAN or WAN links (802.11, T1, T3, Gigabit Ethernet), broadband connections (ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols. The computing device 120 may communicate with other computing devices via any type and/or form of gateway or tunneling protocol such as Secure Socket Layer (SSL) or Transport Layer Security (TLS). The network interface 130 may include a built-in network adapter, network interface card, PCMCIA network card, EXPRESSCARD network card, card bus network adapter, wireless network adapter, USB network adapter, modem or any other device suitable for interfacing the computing device 120 to any type of network capable of communication and performing the operations described herein.

The computing device 120 may operate under the control of an operating system that controls scheduling of tasks and access to system resources. The computing device 120 may be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein.

The computer system 120 can be any workstation, telephone, desktop computer, laptop or notebook computer, netbook, tablet, server, handheld computer, mobile telephone, smartphone or other portable telecommunications device, media playing device, a gaming system, mobile computing device, or any other type and/or form of computing, telecommunications or media device that is capable of communication.

The status of one or more machines 102a-c, 104a-c may be monitored, generally, as part of network management. In one of these embodiments, the status of a machine may include an identification of load information (the number of processes on the machine, CPU and memory utilization), of port information (the number of available communication ports and the port addresses), session status (the duration and type of processes, and whether a process is active or idle), or as mentioned below. In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

The system and method discussed below may be incorporated into one of more of the clients 102a-c, or distributed across a network. For example, the databases discussed below may be in a server remove from a rules/classifier engine that exists at another client or server, and yet another client/server may serve as an interface for users to review and access data generated by the system. Distributing the system across many machines is not required but in any event achieves the desired outcome of improving the performance of the client/servers.

B. Approaches

The system may use one or more of the three approaches described below.

1. Approach 1: Clustering-Based Bootstrapping for Expectation Maximization (CBBEM)

1.1. Overview

This approach may use the Naive Bayes classifier (NB), a classifier in the natural language processing field. Different from the traditional NB, the system algorithm may use both labeled and unlabeled data to train the model by using Expectation-Maximization (EM) algorithm. In addition, the algorithm may create new classes to accommodate samples that can't be explained by existing classes during the learning process. The parameters of the NB model may be saved for incremental learning purpose and the old sample information may not be required in the future. Hence the proposed framework will save both memory and time by updating the clusters incrementally.

1.2 Naive Bayes Classifier

A Naive Bayesian classifier (NBC) is a kind of probabilistic classifier that uses Bayesian rules to tackle classification problems. Naive refers to its assumption that features are independent from each other. $X=(x_1, x_2, x_3, \ldots, x_n)$ is an observation with n features. And there are m target classes $(C_1, C_2, C_3, \ldots, C_m)$. The probability of X coming from class $C_k$ is:

$$p(C_k \mid X = (x_1, x_2, x_3, \ldots, x_n)) = \frac{p(C_k)p(X \mid C_k)}{p(X)} = \frac{p(C_k)\prod_{i=1}^{n} p(x_i \mid C_k)}{\sum_{k=1}^{m} p(C_k)\prod_{i=1}^{n} p(x_i \mid C_k)} \quad \text{Equation 1}$$

where p(•) refers to probability.

The estimated class is:

$$\hat{c} = \operatorname{argmax}_{k \in 1, \ldots, m} p(C_k) \Pi_{i=1}^{n} p(x_i \mid C_k) \quad \text{Equation 2}$$

where $p(x_i \mid C_k)$ refers to the conditional probability of observing feature $x_i$ given the sample is from class $C_k$.

1.3 Expectation-Maximization (EM) Algorithm

An EM algorithm can estimate the parameters in a statistic model. In this case, the framework implements the EM algorithm to estimate the probabilities in the NB model. Assume the parameter set is $\Theta^0$, this yields:

Expectation Step (E step):

$$Q(X) = p(X \mid C, \Theta^{t-1}) \quad \text{Equation 3}$$

where Q(X) is the expected value of the likelihood function estimated by the current parameter set $\Theta^{t-1}$, C and observation X.

Maximization Step (M step):

$$\Theta^t = \operatorname{argmax}_{\Theta} \int_x^{\infty} Q(x) \log p(x, c, \Theta) dx \quad \text{Equation 4}$$

where $\Theta^t$ is the updated parameter set based on expectation.

1.4 Framework

The Clustering Based Bootstrapping for Expectation Maximization (CBBEM) is a proposed incremental classification algorithm. It recurrently trains a Naive Bayesian (NB) Expectation Maximization (EM) algorithm with the help of an unsupervised clustering. The framework first uses the labeled training data to train a Naive Bayesian Classifier model, and uses the EM algorithm to update a decision boundary as new samples arrive. In an Expectation step, the system may classify the new samples by the old classifier. If the new samples can't be classified into any existing classes confidently, they may be transferred to an undetermined data set. A new class may then be created by applying an unsupervised clustering algorithm to the undetermined set. And in Maximization step, the classifier may be updated by the model modified in Expectation step.

Part of the idea of CBBEM http://www.cs.cmu.edu/~bbd/bbd_ecml13.pdf is adapted from a known approach (by Dalvi et al. in a 2013 titled Exploratory Learning publicly available through Carnegie Mellon University, which is incorporated by reference as if fully set forth herein) where a general exploratory semi-supervised learning (SSL) can learn the data when only a fraction of classes is known, the rest of samples may come from novel classes. It solves this problem by using EM algorithm together with a new classification criterion. But the new class criterion is based on if the classifier and may get confused about the affiliation of a new sample. This situation, however, may happen when there are some samples staying between two classes (if the samples are Gaussian distributed for instance) and doesn't necessarily imply the existence of new class. Moreover, the exploratory algorithm may create a new class for only one sample if the sample is picked up by the new class criterion. This may cause a challenge for the NB classifier because it may take the prior probability into account. Only one in a class may be inadequate for NBC model to classify future unlabeled data into this class. Hence, the system improved these issues using a new class criterion and the way this new class was created.

The selection of unsupervised learning clustering algorithm and new class criterion may be based on the use case. For example, assuming the samples are Gaussian distributed, the confidence interval of a sample x can be found using:

$$(x-\mu)^T \Sigma^{-1} (x-\mu) \le X_p^2(\alpha) \quad \text{Equation 5}$$

where p is the degree of freedom, $\mu$ is the centroid of the class which sample x belongs to and $\alpha$ is the probability that a random point falls outside the ellipsoid defined by the equation defined above. We can regard $\alpha$ as the confidence level. And using an unsupervised clustering algorithm, like DBSCAN to find new clusters. FIG. 6 shows the pseudo code of CBBEM.

1.5 Simulated Data Set and Experimental Result

The simulated data set contains 1000 two-dimensional samples drawn from 10 Gaussian distributions, as shown in FIGS. 7A and 7B. FIG. 7A shows the simulated data set visualization. FIG. 7B shows the classification result. All the samples inside the region covered by a same color were classified into the same class by CBBEM algorithm. The algorithm started with an empty training data set and iteratively learn from the unlabeled data set.

The following table compares the performance of CBBEM with the performances of other widely used unsupervised clustering algorithms.

TABLE 1

Performance comparison

|  | ARI | Purity | NMI | Precision | Recall | F-measure |
|---|---|---|---|---|---|---|
| CBBEM | 0.9367 | 0.9710 | 0.9395 | 0.9426 | 0.9432 | 0.9429 |
| DBSCAN | 0.6160 | 0.8370 | 0.7757 | 0.6750 | 0.6320 | 0.6528 |
| k-means | 0.8092 | 0.8770 | 0.8878 | 0.7877 | 0.8750 | 0.8291 |

1.6 DNA Data Set and Experimental Result

First, the ability of novelty detection of this algorithm was evaluated on a DNA sequences classification task. The simulated DNA data set contained 600 sequences from 6 different classes. In this experiment, CBBEM started with an empty training data set and iteratively learned from the unlabeled data set (this is a totally unsupervised case, reads from 6 classes are considered as "novel" because no prior information is provided). The following Table 2 shows the performance of CBBEM and k-means.

TABLE 2

Unsupervised learning experiments

|  | ARI | Purity | NMI | Precision | Recall | F-measure |
|---|---|---|---|---|---|---|
| CBBEM: | 0.6123 | 0.9100 | 0.7259 | 0.8856 | 0.5397 | 0.6619 |
| k-means: | 0.6004 | 0.7650 | 0.6809 | 0.6621 | 0.6718 | 0.6669 |

Second, the incremental learning characteristic of this algorithm was evaluated. There are 3 cases corresponding to different scenarios in practice:

Case 1: Assume all samples from the first 3 classes labeled and available. And all the samples from the rest 3 classes as new unknown data. The algorithm may train NB model on the existing labeled data. And when the new data arrives, it can account for the new data. On the contrary, traditional semi-supervised algorithm like semi-supervised NBC can't account for samples from new classes.

Case 2: Assume half of samples from the first 3 classes are labeled and available, all the rest of samples are unlabeled new data. In this case, the upcoming data contains samples from both existing classes and new classes.

Case 3: Assume half of samples from each class are labeled and available, all the rest of samples as unlabeled new data. In this case, the algorithm is tested in a traditional case that no new class will be presented.

The following Table 3 shows the performances of CBBEM in those three cases:

TABLE 3

Semi-supervised learning experiments

|  | ARI | Purity | NMI | Precision | Recall | F-measure |
|---|---|---|---|---|---|---|
| Case 1: | 0.7404 | 0.9100 | 0.7456 | 0.8295 | 0.8224 | 0.8260 |
| Case 2: | 0.7476 | 0.9133 | 0.7709 | 0.8769 | 0.7175 | 0.7892 |
| Case 3: | 0.8010 | 0.9200 | 0.8347 | 0.8709 | 0.7967 | 0.8322 |

2 Approach 2: Incremental Naive Bayes Learner 2.1 Overview

This proposed algorithm (iNBC) is an incremental version of a Naïve Bayes Classifier for taxonomic classification discussed by Rosen in a 2008 paper called Metagenome Fragment Classification Using N-mer Frequency Profiles, which is available at least at the National Institutes of Health website and incorporated by reference as if fully set forth herein. To be specific, whenever a new labeled sequence is available, the k-mer frequency is added to the existing frequency table if it is from an existing class. Otherwise, a new table is created to accommodate this new class. In this way, re-computation of the k-mer frequency for all existing samples is not needed. Instead, processing the new data to update the model may only be required.

The Naïve Bayes Classifier used in the proposed system is the same as aforementioned Naïve Bayes classifier in section 1.2, Equations 1 and 2. Accommodating new organisms may be computationally expensive for traditional NB model. In previous work, when new data are available, the existing NB model is not used during the updating process which indicates there is a waste of information and efforts in this process. Hence, the incremental NB learner that uses the existing model and new data to update the model may be used. This new method uses the existing model and new data to update the Naive Bayes classifier. And this process doesn't require the access of the existing database any longer and thus requires less memory and computer time during updating.

2.2 Incremental Framework Work-Flow

Figure 8:
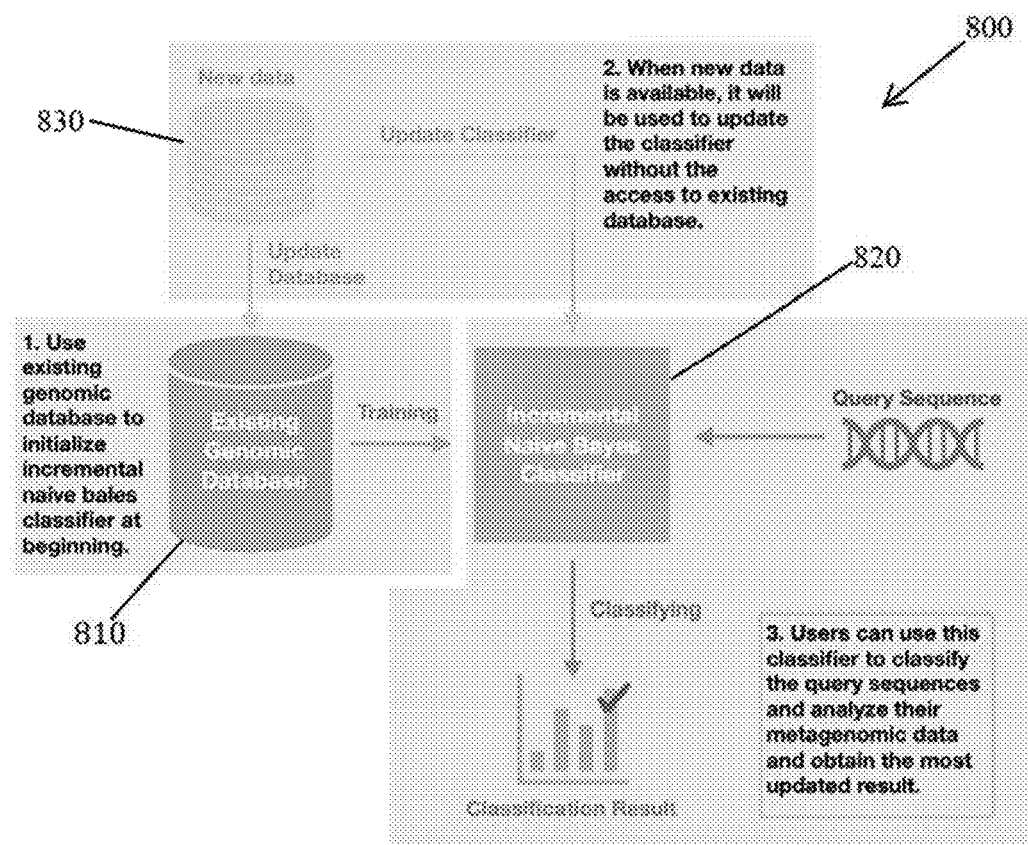
FIG. 8 shows a system diagram of the proposed incremental classifier, iNBC.

FIG. 8 shows the system diagram discussed in more detail below. The first step is using the existing data to train and initialize a NB model, classification result can be generated after the model is initialized.

Second, when new samples arrive, the system will update the NB model based on new data and existing model. New posterior (Equation 1) can be updated based on which classes get updated.

Third, users can use this classifier to classify the query sequences, analyze their metagenomics data and obtain the most updated result.

Add $\alpha$ Smoothing:

When training the NB model, smoothing computes the term frequency and probability:

$$p(x_i \mid C_k) = \frac{N_{x_i, c_k} + \alpha}{V_{c_k} + \alpha \cdot d} \quad \text{Equation 6}$$

where $N_{x_i, C_k}$ is the frequency of word $x_i$ in class $C_k$, $V_{C_k}$ is the total number of words in class $C_k$, d is the total number of unique words in class $C_k$, and $\alpha$ is the smoothing factor that users can tune. Usually, people use $\alpha=1$, i.e., add one smoothing in practice.

2.3 Accuracy Experiment

To demonstrate that this incremental classifier's performance can be improved as more and more data is presented to the classifier, the inventors downloaded all the complete genomes of microorganism from the NCBI website (7,899 complete genomes in total at the time of the experiment). This is labeled by species (2,846 species in total). This database split them into 10 batches randomly. The first batch served as an existing database to initialize the algorithm and the other 9 batches arrived in the system sequentially to mimic the growth of this database. The incremental NBC processed these 9 batches and updated accordingly. Every time the NBC gets updated, the classifier will be evaluated by a simulated testing dataset. This dataset is simulated from the whole genomes microorganism from NCBI website with errors. It contained 789,900 sequences (100 reads per genome). The performance is evaluated on species level as well. FIG. 8 shows the performance of this incremental NBC (iNBC).

FIG. 8 shows a method 800 for updating the taxonomic classifier when new sequences are available, which can improve the performance of the classifier. At beginning, the existing classifier 810 can only correctly classify 50% of the testing sample. But when the iNBC classifier 820 is updated by new batches of data from a new database 830, the accuracy finally reached to around 80%. Another advantage of incremental learning is that when the computer can't load all data available into memory at once, only load a portion of the training data may be loaded into memory, when training on this portion is done, the data can incrementally updates the classifier to load another portion of training data. In this way, the classifier can be trained by all training samples without running out of memory.

2.4 Runtime Experiment

Figure 9:
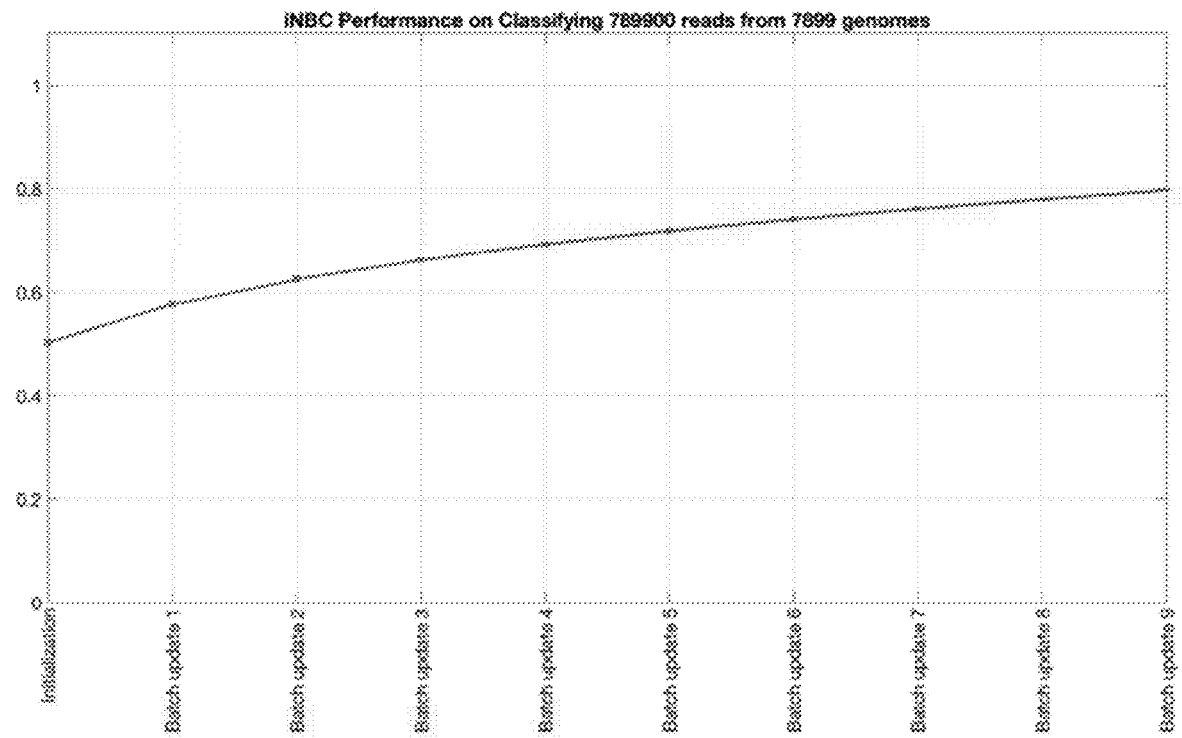
FIG. 9 is a graph showing NCBI broken into 10 batches incremental experiment using iNBC (18-mer was used to train iNBC).

As a proof of concept for the potential performance improvements introduced by incremental learning, the inventors analytically estimated the running times necessary to train their own implementation of Naïve Bayes, capable of building upon existing training sets. They looked at the running time with and without leveraging incremental learning, while training on a dataset with 10 batches. The 10 batches together contain all 7,952 bacteria genomes from NCBI website. In this example, we also simulate the exponential growth of data over 10 batches. FIG. 9 shows that the total number of genomes (y axis) available after adding a new batch to the system (x-axis).

Figure 10:
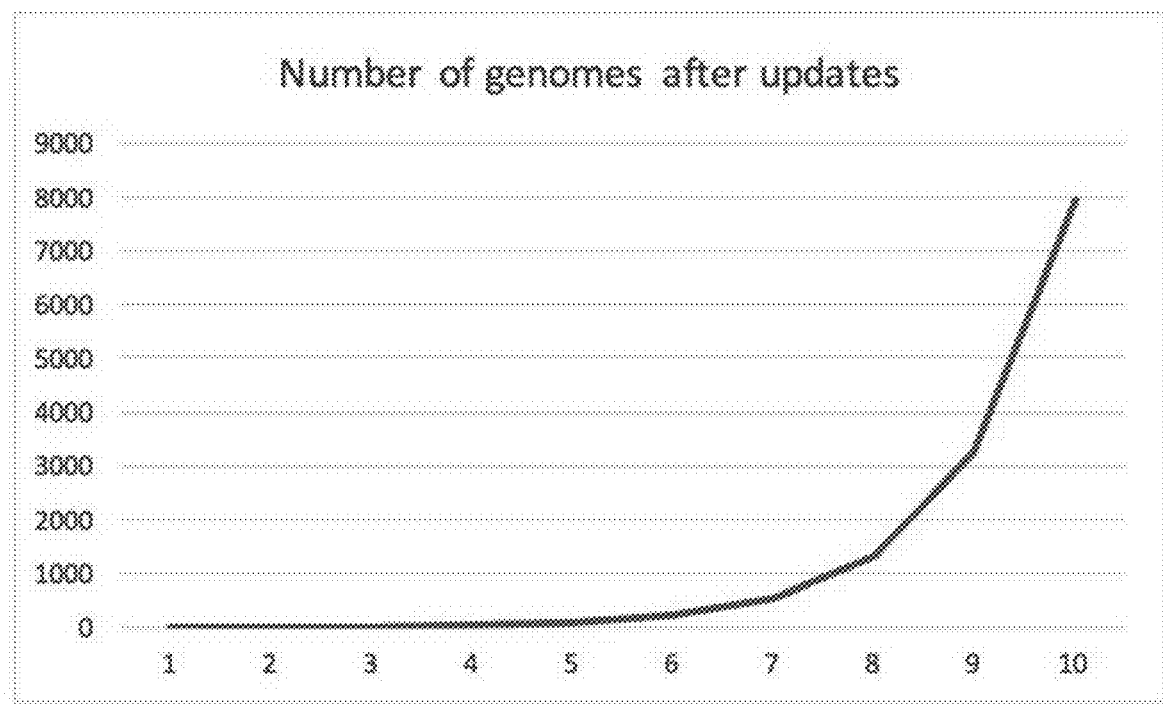
FIG. 10 is a graph showing the total number of genomes per update.

There are two ways to train and update the Naïve Bayes Classifier: (1) train the Naïve Bayes Classifier from scratch and (2) incrementally update the classifier. FIG. 10 compares the estimated time for both update methods.

As shown in the figure, the incremental learning approach is faster than traditional method. After 10 updates, the total amount of time for traditional method is 652.88 min (off the top of the graph) and the incremental learning approach is 387.11 min. A current Amazon™ virtual machine ("i3.4xlarge" with 16 vCPU and 122 GB memory) costs 1.248 dollars per hour as of the date of this application and thus, the incremental learning approach costs 8.05 dollars and traditional method costs 13.58 dollars. The cost will be reduced by around 41% by using incremental learning approach.

Compound this with running a metagenomics data through the classifier, it is common that a few Tera-bases of data take hundreds of CPU hours to process (for example 100 CPU-hours for the dataset considered). If the classifier model is updated with, 1000 genomes to 7,000+ genomes, traditionally, this metagenomics data would need to now be re-classified against all 7,000+ genomes, resulting in 115 hours (for a linear classifier like NBC). But since NBC is linear, a time reduction could be achieved by only classifying the metagenomics data against the NEW 1000 genomes. This would mean only 15 hours of re-processing, instead of 115, saving $125 for just one dataset. A data intensive company would have hundreds, if not thousands of datasets, resulting in savings of many thousands of dollars. And moreover, allowing the company to keep data/databases updated weekly if not more often. In the known methods, a user might only want to update databases on a semi-annual basis, which would lead to less accurate and outdated results.

3. Approach 3: Incremental k-Mer Based Metagenome Fragment Classifier

3.1 Overview

Figure 12:
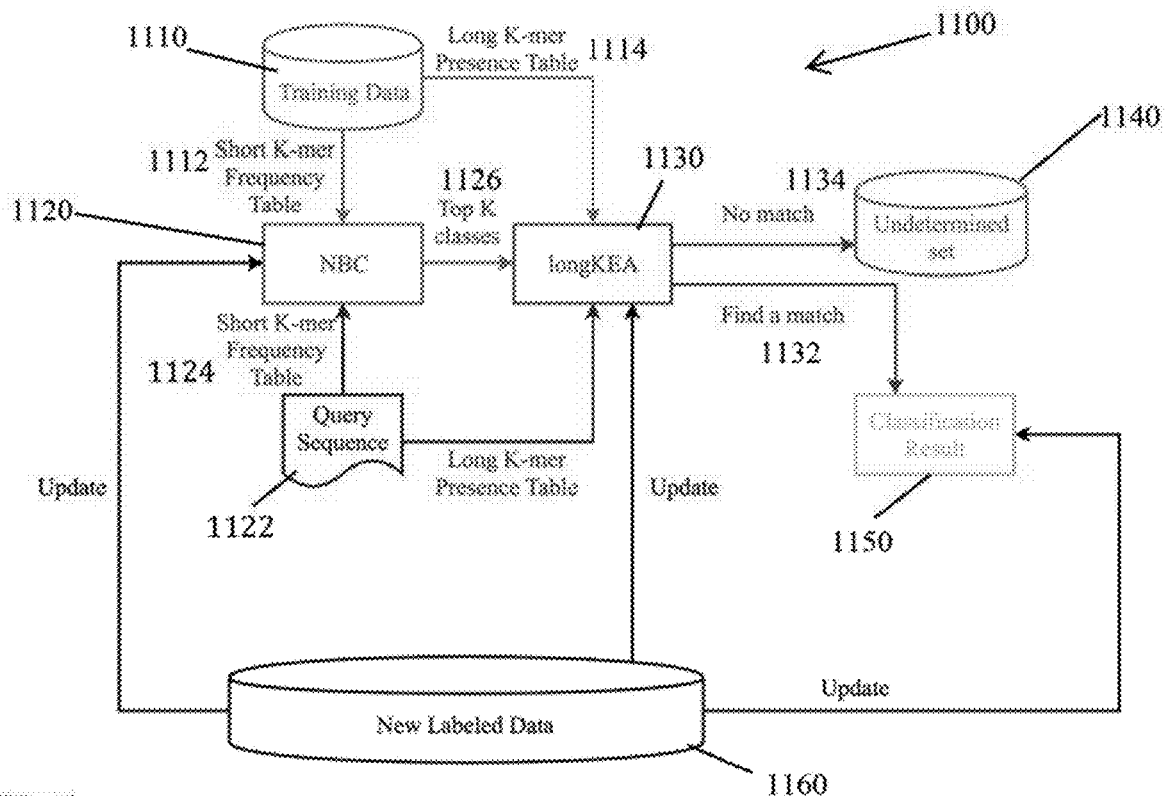
FIG. 12 shows one of the proposed system diagram, iKMF.
Figure 13:
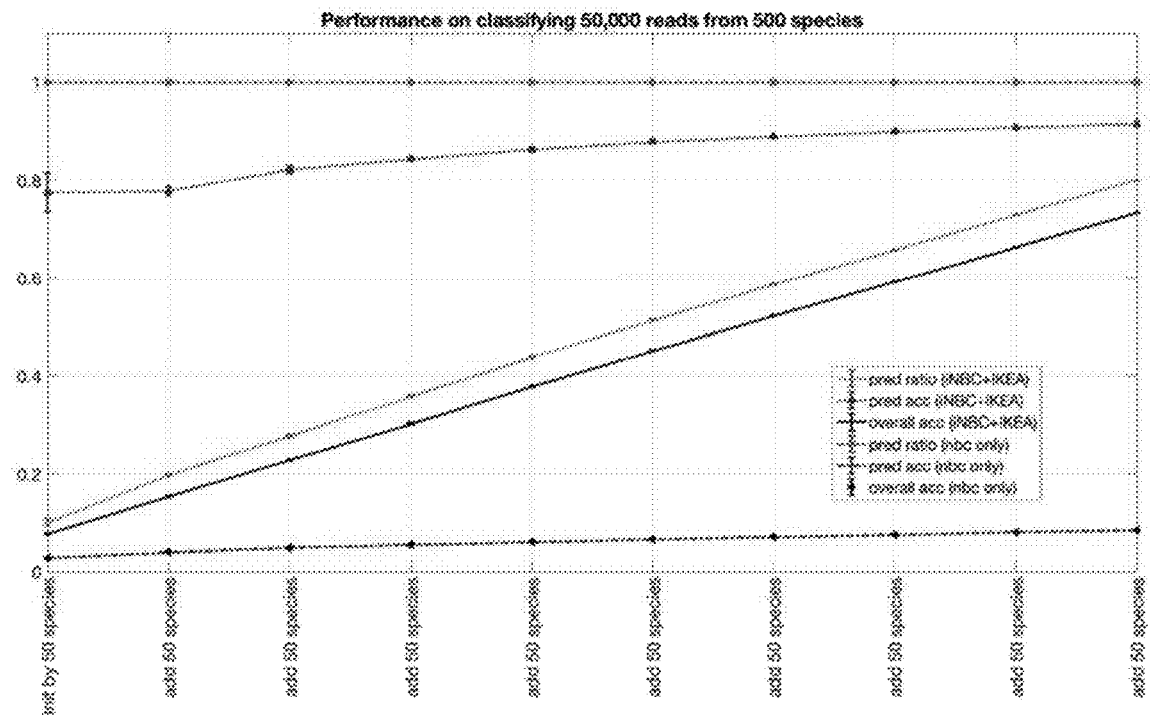
FIG. 13 is a graph showing the evaluation of the proposed system, iKMF.

To further improve the accuracy of this incremental taxonomic classifier, an incremental k-mer based metagenome fragment classifier (iKMF) may be used. This classifier uses Naïve Bayes Classifier and long k-mer exact alignment to classify query sequence. As shown in FIG. 12, even though some testing samples are from novel species that Naïve Bayes Classifier has not been trained on yet, the classifier will classify these samples into one of existing class. Hence, the accuracy is not good at the very beginning. In practice, when encountering some novel samples or error samples, NB may not be able to handle them correctly and may introduce error into the analysis. Long k-mer exact alignment has been proven to be accurate in taxonomic classification in a previous work called Kraken (in a 2014 paper by Wood called Kraken: Ultrafast Metagenomic Sequence Classification Using Exact Alignments, which is available on the biomedcentral website and incorporated by reference as if fully set forth herein) in which Kraken has shown that a classifier can leave some samples unclassified if the classifier is not confident enough about the classification result. However, Kraken is not an incremental learner, like the proposed incremental version of Naïve Bayes classifier. Thus, the combination of the NBC and long k-mer exact alignment may build a more accurate incremental taxonomic classifier.

3.2 Framework

Figure 11:
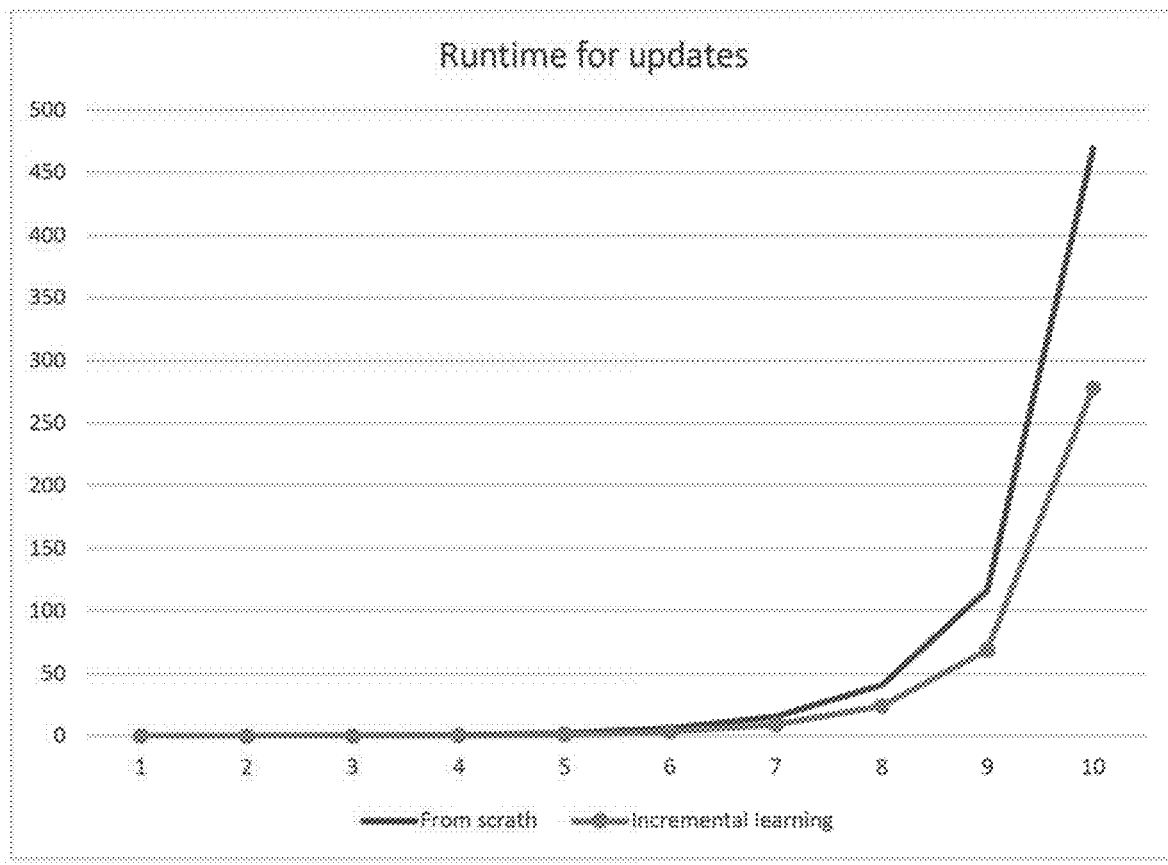
FIG. 11 is a graph showing the runtime of incremental learning per update versus runtime of no incremental learning

This framework may use two components: NB model (Naïve Bayes Classifier) and longKEA (Long k-mer exact alignment, inspired by Kraken. This mechanism may help NBC improve accuracy as well as detect undetermined query sequences, possibly reads from a novel species). FIG. 11 shows a system diagram for iKMF 1100. In the training phase using training data 1110, the whole genome sequences yield a short k-mer frequency table 1112 and a long k-mer presence table 1114. The former is used to train NBC 1120 and the latter is stored in a longKEA database 1130 with respect to their labels. In the testing phase, a query sequence 1122 is first classified by the NBC 1120 in a short K-mer frequency table 1124. Then, the top K classes 1126 that give rise to highest posteriors will be exterminated deeper by the longKEA system 1130. To be specific, the class that has highest number of long k-mers in common with the query sequence will the predicted class 1132 resulting in a classification result 1150. If none of the long k-mers from the query sequence can be found 1134 in longKEA, the query sequence will be left in an undetermined set 1140. When new training data 1160 is available, both the NBC 1120 and the longKEA 1130 can be updated quickly without reprocessing the whole training dataset.

3.3 Experiment

To evaluate the performance of this system, a subset of the NCBI database may be used to create some experimental data. This experimental data included 500 species. These 500 species were split into 10 batches. Each batch exclusively contains all the genomes from 50 species. The classifier was initialized by one batch, the rest of 9 batches were used to update the classifier in a sequential order (batch updates). After each update, the classifier was evaluated by a testing dataset. The training process was repeated 10 times by rotating the initialization batch. The variances and means of the performance were recorded. Testing dataset used in this experiment contained 50,000 simulated reads (100 reads/species). The performance of non-incremental NBC (using short k-mer) was also evaluated and presented as a baseline. Accuracy is the major metric for our evaluation. However, since the proposed system may leave "not sure" reads unclassified. So, these reads will be assigned to class '−1'. FIG. 12 shows the performance of this test. The percentage of reads that were classified is shown in figure as "pred ratio". The accuracy of the reads that were predicted is shown in figure as "pred acc". And the accuracy of all the reads is shown as "overall acc".

In FIG. 12, the solid lines represent the performance of incremental learner and the dotted lines represent the performance of non-incremental version NBC. Not that only the NBC has to be retrained in every batch updates, it also forces the testing data being classified into one of the existing class (red dotted line, i.e., predicted ratio, is 100% over 10 batches while some testing reads are from novel classes that have never been seen by the classifier). The incremental learner, on the other hand, only classified a small portion of the testing data at the beginning and increases the portion of classified data over time given more and more labeled data are used to update the classifier (the solid line, i.e., predicted ratio, is increasing over time according to batch updates). The accuracy of predicted reads is hence maintained at a high level. As more and more data being presented to the classifier, the variance of predicted accuracy is also reduced, which indicates that the incremental learner got constantly improved over batch updates. The overall accuracy also supports this observation

4. A Related Publication and Use Case

4.1 Overview

Author Name disambiguation in digital libraries is a challenging task as the number of ambiguous names and new publications that might be associate with them is growing exponentially and accurate authorship is essential to many modern classification, search, recommendations, and categorization tasks. The inventors developed an incremental learning framework based on High Precision rules (HP) (HP is discussed by Levin and Krawcyk in their 2012 paper titled Citation-Based Bootstrapping for Large-Scale, which is incorporated by reference as if fully set forth herein and available at the Stanford University publications page on the Internet) and the Naive Bayes Classifier (NB) to disambiguate author names in large-scale scientific citation databases as well as update the disambiguation results when new publications are added to the database.

4.2 Framework

Figure 14:
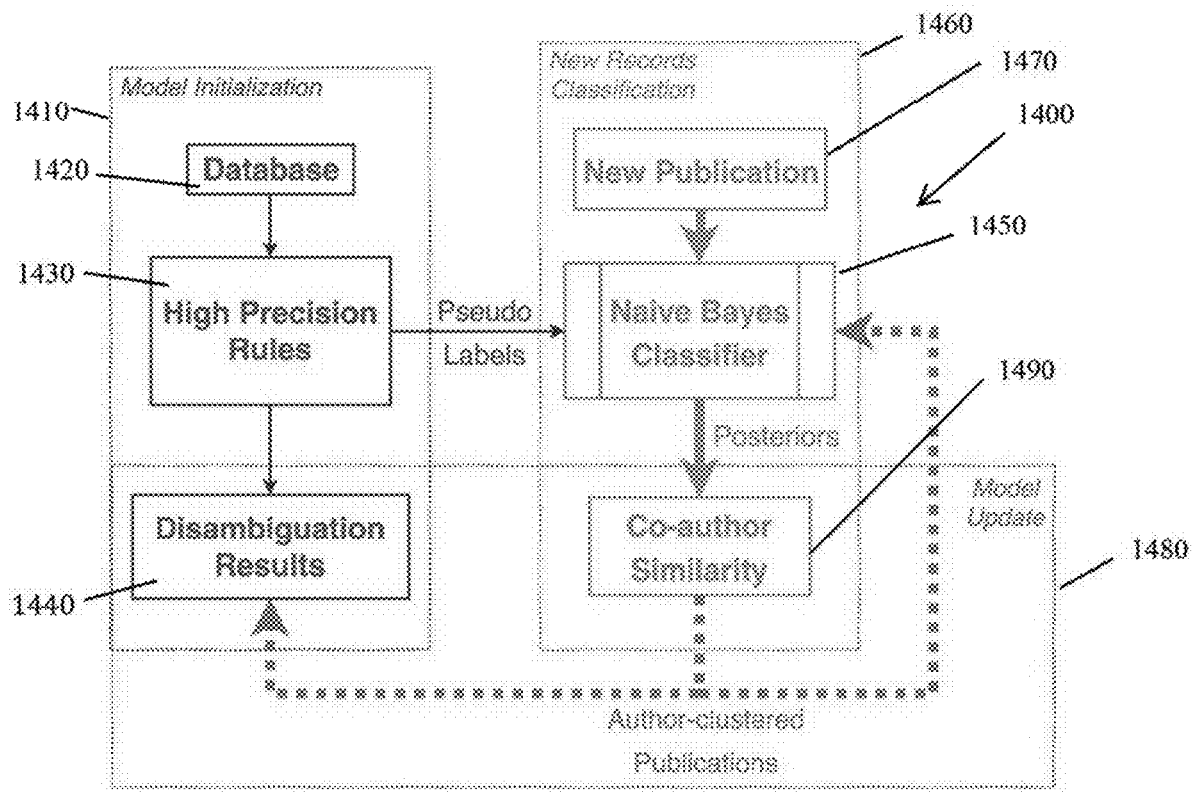
FIG. 14 shows a system diagram of the incremental learning framework based on High Precision rules.

The method has three main stages: model initialization, new record classification, and model updating. FIG. 14 shows a system diagram of the incremental learning framework based on High Precision rules 1400. In the model initialization stage 1410, if there are no existing disambiguation results available from a source database 1420, this method uses HP rules 1430 to generate pseudo-labeled data and high precision clusters from the existing dataset. If results are available, the model will instead adopt the clustering information from the existing disambiguated database 1140. Then an NB classifier 1450 is trained to create a probabilistic model representation for each cluster.

In the second new records classification stage 1460, when a new citation/data record is available 1470, the NB classifier 1450 will compute the posterior probability of the record given each existing cluster. The clusters obtaining top posterior scores will be investigated by computing the coauthor similarities:

$$J(Au_i, C_k) = \max_{c_k} \left\{ \frac{|Au_i \cap Au_{c_{k,j}}|}{|Au_i \cap Au_{c_{k,j}}|} \right\} \quad \text{Equation 7}$$

where $Au_i$ refers to the list of coauthors of new citation record i. $Au_{C_{k_j}}$ is the list of coauthors of a citation record in cluster $C_k$. And $C_k$ refers to a citation cluster generated by the algorithm that contains the citation records written by the same author.

In the third stage, based on the result from stage 2 1460, the system will determine if the record belongs to an existing cluster or a new one. The disambiguation result and NB classifier will be updated based on the decision in the model update stage 1480 that determines co-author similarity 1490. When deciding whether to create a new cluster to accommodate new records or not, the proposed algorithm is conservative. It generally creates more clusters than necessary, but the purity of each cluster is high. This choice is reasonable since in a digital library, human correction is often an additional post-processing option. Hence, it is easier for humans to manually select and merge several clusters than to select correct individual papers from clusters and then place them together.

4.3 Experiment

For this use case, inventors tested two real-world datasets to evaluate the framework. The first was a publicly available subset from BDBcomp and the second was a proprietary dataset provided by Clarivate Analytics Web of Science (CAWoS). Performance on the two datasets were used to compare the proposed algorithm against the implementations of INDi and INC, two incremental author disambiguation methods proposed by A. Carvalho and A. Santana, respectively and representing the current state of the art.

For experiments on the BDBcomp dataset, the inventors first split the publications into name blocks according to the authors' last name and first initial. For the authors in each name block with only one paper (which was about 15 authors per block on average) in BDBComp, the inventors selected 4 authors to be included in the incremental testing dataset while the rest were used to initialize the algorithm. For the authors having more than one paper, the inventors included half the citations (rounded down) during initialization and the remainder for testing. Table 4, Table 5 shows performance on various authors in BDBcomp dataset with INDi and INC and Table 6 with the proposed method.

TABLE 4

| INDi Performance ($\alpha_{title} = 0$, $\alpha_{venue} = 0.1$, $\delta = 0.4$) | | | | | | |
|---|---|---|---|---|---|---|
| Block | Precision | Recall | F-measure | ACP | AAP | K |
| a oliveira | 0.96 | 0.13 | 0.23 | 0.98 | 0.53 | 0.72 |
| a silva | 0.86 | 0.12 | 0.21 | 0.98 | 0.69 | 0.82 |

TABLE 4-continued

INDi Performance ($\alpha_{title} = 0$, $\alpha_{venue} = 0.1$, $\delta = 0.4$)

| Block | Precision | Recall | F-measure | ACP | AAP | K |
|---|---|---|---|---|---|---|
| f silva | 1 | 0.16 | 0.29 | 1 | 0.84 | 0.92 |
| j oliveira | 1 | 0.41 | 0.59 | 1 | 0.70 | 0.83 |
| j silva | 0.89 | 0.14 | 0.25 | 0.97 | 0.61 | 0.77 |
| j souza | 1 | 0.06 | 0.12 | 1 | 0.40 | 0.64 |
| l silva | 1 | 0.24 | 0.39 | 1 | 0.67 | 0.82 |
| m silva | 0.5 | 0.20 | 0.29 | 0.95 | 0.81 | 0.88 |
| r santos | 1 | 0.67 | 0.80 | 1 | 0.95 | 0.97 |
| r silva | 0.67 | 0.33 | 0.44 | 0.96 | 0.88 | 0.92 |

TABLE 5

INC Performance ($\omega_a = 3$, $\omega_c = 3$, $\omega_t = 1$, $\omega_v = 1$, $\gamma = 2$)

| Block | Precision | Recall | F-measure | ACP | AAP | K |
|---|---|---|---|---|---|---|
| a oliveira | 0.90 | 0.31 | 0.47 | 0.88 | 0.61 | 0.73 |
| a silva | 0.75 | 0.37 | 0.49 | 0.89 | 0.81 | 0.85 |
| f silva | 0.55 | 1 | 0.71 | 0.84 | 1 | 0.92 |
| j oliveira | 0.88 | 0.39 | 0.54 | 0.94 | 0.70 | 0.81 |
| j silva | 0.67 | 0.39 | 0.49 | 0.83 | 0.76 | 0.80 |
| j souza | 0.88 | 0.26 | 0.40 | 0.88 | 0.55 | 0.70 |
| l silva | 0.65 | 0.52 | 0.58 | 0.81 | 0.84 | 0.82 |
| m silva | 0.36 | 0.80 | 0.50 | 0.73 | 0.95 | 0.83 |
| r santos | 0.50 | 1 | 0.67 | 0.85 | 1 | 0.92 |
| r silva | 0.33 | 0.5 | 0.40 | 0.81 | 0.91 | 0.86 |

TABLE 6

Proposed method Performance ($\epsilon = 10$, $\theta = 0.35$)

| Block | Precision | Recall | F-measure | ACP | AAP | K |
|---|---|---|---|---|---|---|
| a oliveira | 0.98 | 0.27 | 0.42 | 0.98 | 0.60 | 0.77 |
| a silva | 0.97 | 0.29 | 0.44 | 0.98 | 0.76 | 0.86 |
| f silva | 0.86 | 1 | 0.92 | 0.96 | 0.76 | 0.86 |
| j oliveira | 0.90 | 0.78 | 0.83 | 0.94 | 0.89 | 0.91 |
| j silva | 0.81 | 0.38 | 0.51 | 0.90 | 0.73 | 0.81 |
| j souza | 1 | 0.21 | 0.35 | 1 | 0.52 | 0.72 |
| l silva | 1 | 0.55 | 0.71 | 1 | 0.85 | 0.92 |
| m silva | 1 | 0.80 | 0.89 | 1 | 0.95 | 0.97 |
| r santos | 1 | 0.67 | 0.80 | 1 | 0.95 | 0.97 |
| r silva | 0.75 | 0.50 | 0.60 | 0.96 | 0.91 | 0.94 |

Figure 15:
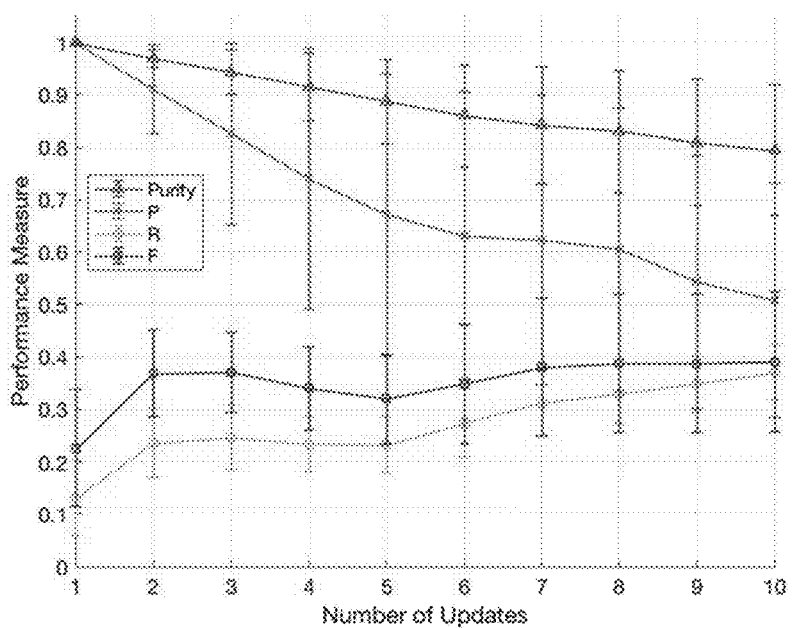
FIG. 15 is a graph showing CAWoS broken into 10 batches incremental experiment using INDi (parameters: $\alpha_{title}=0$, $\alpha_{venue}=0.1$, $\delta=0.6$).

For experiments on CAWoS, the inventors split the 19,877 citations from the CAWoS test dataset into 10 batches ensuring that each batch included 72 labeled citations. The first batch served as the existing citation library to initialize the algorithm and the other 9 batches arrived in the system sequentially. The incremental algorithm processed these 9 batches and updated accordingly. The experiments were conducted 10 times. Each experiment was initialized by a fold of the data and updated by the rest of the batches. The mean and standard deviation of the performance for the ten experiments was computed. The INDi's and INC's performance on the CAWoS data over time is shown in FIGS. 14 and 15, and the proposed method's performance is shown in FIG. 16.

Table 6 shows that the proposed incremental learning algorithm is superior in terms of the K-measure (a geometric mean of ACP and AAP) and yields better (6 out of 10 author blocks) disambiguation results in terms of F-measure and precision as compared to the current state of the art. As shown in the tables, the INDi algorithm can produce more pure clusters (highest ACP in 9 out of 10 author blocks) than our proposed algorithm at the cost of lower Recall and AAP. In fact, there is a trade-off between precision and recall as it switches from clustering some citation records alone in their own clusters, to grouping similar citations with fewer clusters.

Figure 16:
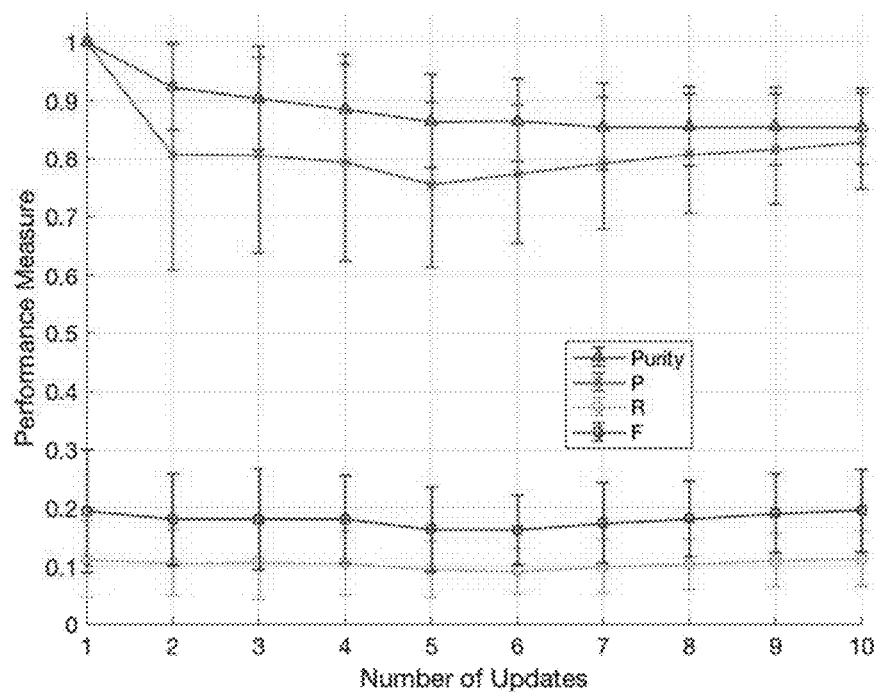
FIG. 16 is a graph showing CAWoS broken into 10 batches incremental experiment using INC (parameters: $\omega_a=3$, $\omega_c=3$, $\omega_t=1$, $\omega_v=1$, and $\gamma=2$).
Figure 17:
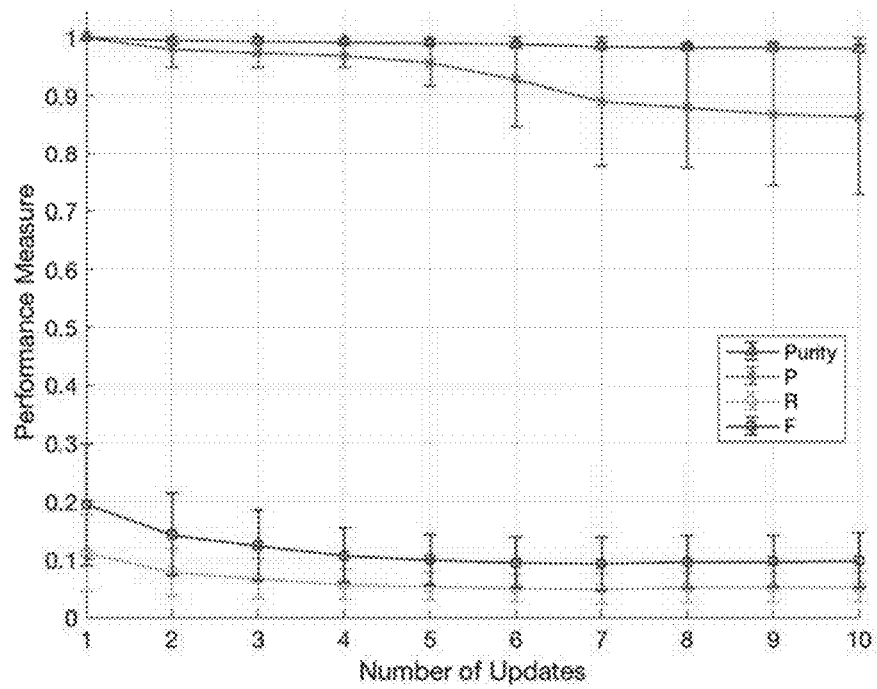
FIG. 17 is a graph showing CAWoS broken into 10 batches incremental experiment using proposed method (parameters: $\varepsilon=100$, $\theta=0.35$).

FIG. 16 shows the performance of the proposed algorithm over time by simulating the new citation arrival in the CAWoS dataset. The proposed algorithm, using the θ derived from BDBComp dataset, no longer achieves the highest F-measure (due to poor recall) but maintains its high precision performance. This may indicate that larger datasets may need different parameters to mitigate recall performance loss. Also, for the CAWoS data, the proposed algorithm's performance does not vary as much as INC/INDi's resulting in tighter error bars. This indicates that the algorithm is more robust and less dependent on the initialization batch than other methods.

The results are fine-tuned to this data but could easily be extended to work on nearly any structured or semi-structured (XML, JSON, text, etc.) digital dataset.

In sum, the incremental learning concepts have been verified by many real datasets and practical problems in Natural Language Processing as well as the Bioinformatics field. The above experiments and use cases have shown the efficiency of the incremental learning algorithm. The performance of supervised incremental learning algorithm was improved as more and more training data was presented to the classifier. The system herein also converted a traditional taxonomic classifier, to a supervised incremental learner.

While the invention has been described regarding the embodiments above, a person of ordinary skill in the art would understand that various changes or modifications may be made thereto without departing from the scope of the claims.

The invention claimed is:

1. A system for classifying samples comprising:
   a processor, a memory accessible by the processor, and computer instructions stored in the memory and executable by the processor to perform:
   store a pre-existing training data cluster;
   apply a Naive Bayes Classifier (NBC) to data within the training data cluster; receive new data; and
   apply the NBC to the new data based on the NBC applied to training data;
   wherein the NBC includes a classification algorithm used to classify the data with the NBC;
   wherein the classification algorithm uses classification criterion to determine NBC, and
   wherein the classification algorithm is updated based on the training data and receipt of the new data,
   wherein updating of the classification algorithm is done using an Expectation-Maximization (EM) algorithm that estimates the NBC being accurately applied to the data, wherein the EM algorithm includes an Expectation Step applying a formula:

$Q(X) = p(X|C, \Theta^{t-1})$, wherein the EM algorithm includes a Maximization Step applying a formula:

$\Theta^t = \mathrm{argmax}_\Theta \int_x^\infty Q(x) \log p(x, c, \Theta) dx$;

wherein updating of the NBC includes using a framework based on High Precision rules to classify the data, wherein the High Precision rules generate pseudo-labeled data and high precision clusters from existing datasets comprising at least a simulated testing dataset and based on the pseudo-labeled data, the NBC is trained to create a probabilistic model representation for each data cluster, wherein $X=(x_1, x_2, x_3, \ldots x_n)$ is an observation with n features, and there are m target classes $(C_1, C_2, C_3, \ldots C_m)$;

where Q(x) represents an expected value of a likelihood function estimated by current parameter set, $\Theta^{t-1}$, C, and observation X, and where $\Theta^t$ is the updated parameter set based on expectation.

2. The system of claim 1, wherein updating of the NBC—includes a term frequency and probability calculation accomplished according to a formula:

$$p(x_i \mid C_k) = \frac{N_{x_i, c_k} + \alpha}{V_{c_k} + \alpha \cdot d}$$

where $N_{x_i}C_k$ is a frequency of word $x_i$ in class Ck, $V_{C_k}$ is a total number of words in class $C_k$, d is a total number of unique words in the class $C_k$ and $\alpha$ is a smoothing factor that users can tune.

3. The system of claim 1, further identify some of the new data as not able to be classified, and add the new data to an undetermined data set.

4. The system of claim 1, wherein the updating of the NBC includes using an incremental k-mer based metagenome fragment classifier (iKMF) to classify the data.

5. The system for claim 1 performed by a client.

6. A method for classifying samples, wherein the method comprises:
    storing a pre-existing training data cluster;
    applying a Naive Bayes Classifier (NBC) to data within the training data cluster;
    receiving new data; and
    applying the NBC to the new data based on the NBC applied to training data;
    wherein the NBC-includes a classification algorithm used to classify the data with the NBC,
    wherein the classification algorithm uses classification criterion to determine the NBC, and
    wherein the classification algorithm is updated based on the training data and receipt of the new data,
    wherein updating of the classification algorithm is done using an Expectation-Maximization (EM) algorithm that estimates the NBC being accurately applied to the data, wherein the EM algorithm includes an Expectation Step applying a formula:

$$Q(X) = p(X \mid C, \Theta^{t-1}),$$

wherein the EM algorithm includes a Maximization Step applying a formula:

$$\Theta^t = \mathrm{argmax}_\Theta \int_x^\infty Q(x) \log p(x, c, \Theta) dx;$$

wherein updating of the NBC includes using a framework based on High Precision rules to classify the data, wherein the High Precision rules generate pseudo-labeled data and high precision clusters from existing datasets comprising at least a simulated testing dataset and based on the pseudo-labeled data, the NBC is trained to create a probabilistic model representation for each data cluster, wherein:
$X=x_1, x_2, x_3, \ldots x_n)$ is an observation with n features, and there are m target classes $(C_1, C_2, C_3, \ldots C_m)$;

where Q(x) represents an expected value of a likelihood function estimated by current parameter set, $\Theta^{t-1}$, C, and observation X, and where $\Theta^t$ is the updated parameter set based on expectation.

7. The method of claim 6, wherein updating of the NBC-includes a term frequency and probability calculation accomplished according to a formula:

$$p(x_i \mid C_k) = \frac{N_{x_i, c_k} + \alpha}{V_{c_k} + \alpha \cdot d}$$

where $N_{x_i, C_k}$ is a frequency of word $x_i$ in class $C_k$, $V_{C_k}$ is a total number of words in class $C_k$, d is a total number of unique words in the class $C_k$ and $\alpha$ is a smoothing factor that users can tune.

8. The method of claim 6, wherein the method identify some of the new data as not able to be classified, and add the new data to an undetermined data set.

9. The method of claim 6, wherein the updating of the NBC-includes using an incremental k-mer based metagenome fragment classifier (iKMF) to classify the data.

10. The method for claim 6, wherein the method is performed by a client.

\* \* \* \* \*